United States Patent
Wilson et al.

(10) Patent No.: US 10,232,151 B2
(45) Date of Patent: Mar. 19, 2019

(54) MULTI-LUMEN VENTRICULAR DRAINAGE CATHETER

(71) Applicant: INTEGRA LIFESCIENCES SWITZERLAND SÀRL, Le Locle (CH)

(72) Inventors: Stephen Wilson, N. Easton, MA (US); Emilie Neukom, Zug (CH)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 965 days.

(21) Appl. No.: 14/182,997

(22) Filed: Feb. 18, 2014

(65) Prior Publication Data

US 2014/0228734 A1   Aug. 14, 2014

Related U.S. Application Data

(63) Continuation of application No. 12/894,111, filed on Sep. 29, 2010, now abandoned.

(51) Int. Cl.
*A61M 25/00* (2006.01)
*A61M 27/00* (2006.01)

(52) U.S. Cl.
CPC ........ *A61M 27/006* (2013.01); *A61M 25/007* (2013.01); *A61M 25/0071* (2013.01); *A61M 2205/04* (2013.01); *A61M 2210/0693* (2013.01)

(58) Field of Classification Search
CPC ............ A61M 25/007; A61M 25/0071; A61M 27/006; A61M 2205/04; A61M 2210/0693
See application file for complete search history.

(56) References Cited

U.S. PATENT DOCUMENTS

| 4,182,343 A | 1/1980 | Inaba |
| 4,375,816 A | 3/1983 | Labianca |
| 4,377,169 A | 3/1983 | Banks |
| 4,398,910 A | 8/1983 | Blake |
| 4,406,656 A | 9/1983 | Hattler |
| 4,465,481 A | 8/1984 | Blake |
| 4,465,482 A | 8/1984 | Tittel |

(Continued)

FOREIGN PATENT DOCUMENTS

| DE | 3033459 A1 | 4/1982 |
| EP | 1712252 A1 | 10/2006 |

(Continued)

OTHER PUBLICATIONS

U.S. Appl. No. 12/894,111, Non-Final Rejection dated Oct. 18, 2013.

(Continued)

*Primary Examiner* — Adam Marcetich
(74) *Attorney, Agent, or Firm* — Troutman Sanders LLP

(57) ABSTRACT

A shunt includes a housing having an inlet, an outlet and a flow control mechanism disposed within the housing. A ventricular catheter is connected to the inlet of the housing. The catheter has a longitudinal length, a proximal end, a distal end, and an inner lumen extending therethrough. The inner lumen of the catheter includes at least two lumens at the distal end and has only one lumen at the proximal end. The catheter has one slit and aperture corresponding to each of the at least two lumens located at the distal end of the catheter.

2 Claims, 3 Drawing Sheets

(56) References Cited

U.S. PATENT DOCUMENTS

| | | | |
|---|---|---|---|
| 4,610,671 A | 9/1986 | Luther | |
| 4,655,745 A | 4/1987 | Corbett | |
| 4,767,400 A | 8/1988 | Miller | |
| 4,795,439 A | 1/1989 | Guest | |
| 4,863,441 A | 9/1989 | Lindsay | |
| 4,950,232 A | 8/1990 | Ruzicka | |
| 4,961,729 A | 10/1990 | Vaillancourt | |
| 4,973,319 A * | 11/1990 | Melsky | A61M 25/0075 137/860 |
| 5,116,310 A | 5/1992 | Seder | |
| 5,201,723 A | 4/1993 | Quinn | |
| 5,207,684 A | 5/1993 | Nobles | |
| 5,360,414 A | 11/1994 | Yarger | |
| 5,405,316 A | 4/1995 | Magram | |
| 5,531,673 A | 7/1996 | Helenowski | |
| 5,776,096 A | 7/1998 | Fields | |
| 6,582,388 B1 | 6/2003 | Coleman | |
| 6,821,265 B1 | 11/2004 | Bertolero | |
| 6,866,657 B2 | 3/2005 | Shchervinsky | |
| 6,893,424 B2 | 5/2005 | Shchervinsky | |
| 7,037,288 B2 | 5/2006 | Rosenberg | |
| 7,090,672 B2 | 8/2006 | Underwood | |
| 7,094,214 B2 | 8/2006 | Dextradeur | |
| 7,195,608 B2 | 3/2007 | Burnett | |
| 7,207,965 B2 | 4/2007 | Simon | |
| 7,223,263 B1 | 5/2007 | Seno | |
| 7,226,441 B2 | 6/2007 | Kulessa | |
| 7,604,658 B2 | 10/2009 | Wilson | |
| 7,959,623 B2 | 6/2011 | Massengale | |
| 2003/0135148 A1 | 7/2003 | Dextradeur | |
| 2003/0236483 A1 | 12/2003 | Ren | |
| 2005/0159697 A1 | 7/2005 | Dextradeur | |
| 2005/0251144 A1 | 11/2005 | Wilson | |
| 2009/0118661 A1 | 5/2009 | Moehle | |
| 2009/0254062 A1 | 10/2009 | McGlothlin | |
| 2011/0172590 A1 * | 7/2011 | Akahoshi | A61F 9/00745 604/22 |

FOREIGN PATENT DOCUMENTS

| | | |
|---|---|---|
| GB | 2089215 A | 6/1982 |
| JP | 2002-224222 A | 8/2002 |

OTHER PUBLICATIONS

U.S. Appl. No. 12/894,111, Non-Final Rejection dated Mar. 22, 2012.

U.S. Appl. No. 12/894,111, Final Rejection dated Jul. 20, 2012.

* cited by examiner

FIG. 3
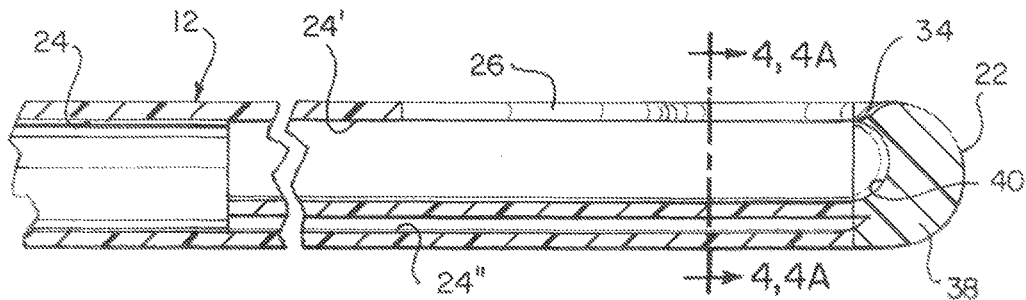
FIG. 4 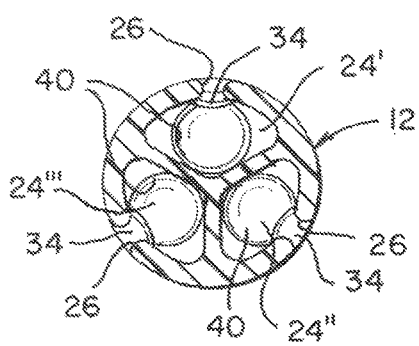 FIG. 4 A 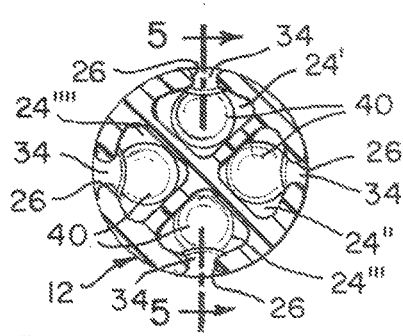
FIG. 5
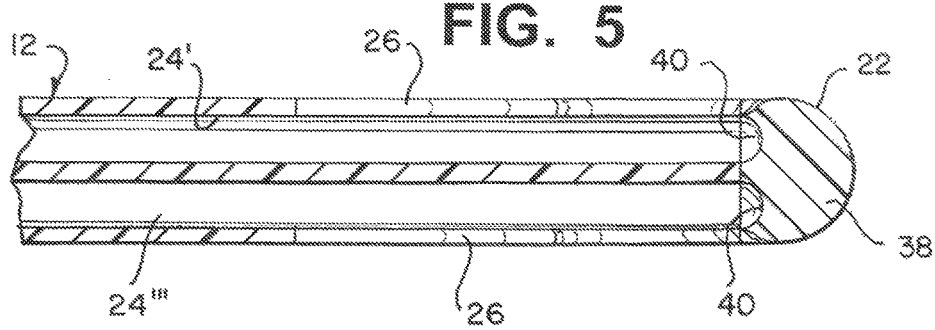
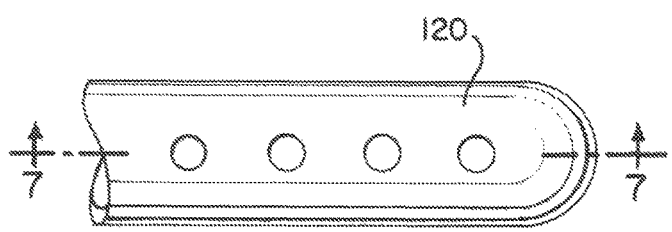
FIG. 6
PRIOR ART

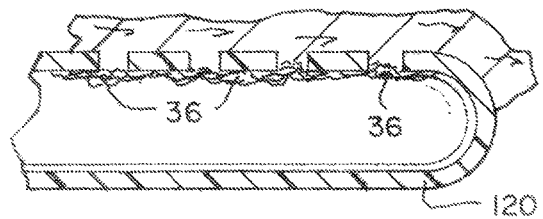
FIG. 7
PRIOR ART
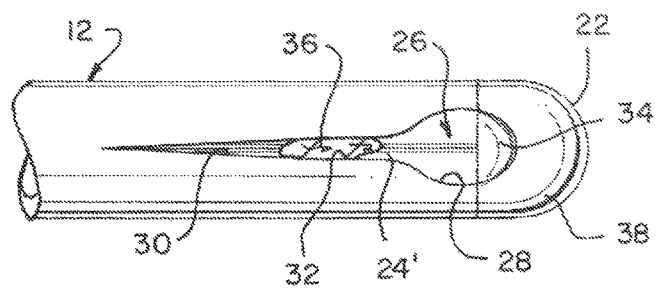
FIG. 8 A
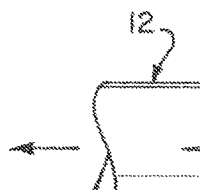
FIG. 8 B
FIG. 9
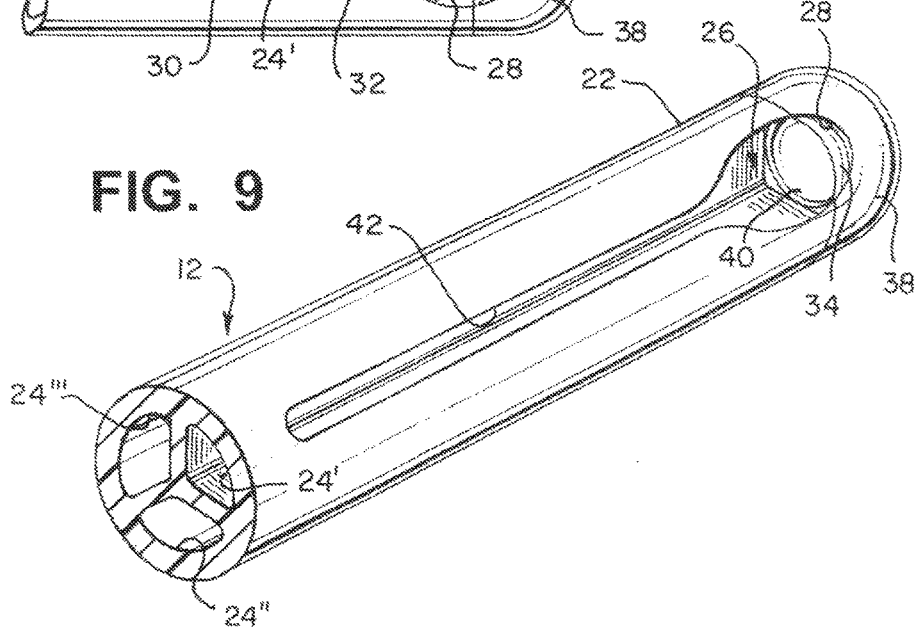

MULTI-LUMEN VENTRICULAR DRAINAGE CATHETER

CROSS REFERENCE TO RELATED APPLICATION

The present application is a continuation of U.S. application Ser. No. 12/894,111 filed Sep. 29, 2010.

FIELD OF THE INVENTION

The present invention relates generally to a shunt and a catheter having a system for reducing the risk of blockage or obstruction of the catheter apertures and also increases the ease of revision surgery if the catheter is removed.

BACKGROUND OF THE INVENTION

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intraventricular or intracranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or apertures positioned along the length of the ventricular catheter to allow the CSF to enter into the shunt system, as shown in FIGS. 6 and 7.

Shunting is considered one of the basic neurosurgical procedures, yet it has the highest complication rate. The most common complication with shunting is obstruction of the system. Although obstruction or clogging may occur at any point along the shunt system, it most frequently occurs at the ventricular end of the shunt system. While there are several ways that the ventricular catheter may become blocked or clogged, obstruction is typically caused by growth of tissue, such as the choroid plexus, around the catheter and into the apertures, as shown in FIG. 7. The apertures of the ventricular catheter can also be obstructed by debris, bacteria, or coagulated blood.

Some of these problems can be treated by backflushing, which is a process that uses the CSF present in the shunt system to remove the obstructing matter. This process can be ineffective, however, due to the small size of the apertures of the ventricular catheter and due to the small amount of flushing liquid available in the shunt system. Other shunt systems have been designed to include a mechanism for flushing the shunt system. For example, some shunt systems include a pumping device within the system which causes fluid in the system to flow with considerable pressure and velocity, thereby flushing the system. As with the process of backflushing, using a built-in mechanism to flush the shunt system can also fail to remove the obstruction due to factors such as the size of the apertures and the degree and extent to which the apertures have been clogged.

Occluded ventricular catheters can also be repaired by cauterizing the catheter to remove blocking tissue, thereby reopening existing apertures that have become occluded. Alternatively, new apertures can be created in the catheter. These repairs, however, may be incapable of removing obstructions from the ventricular catheter depending on the location of the clogged apertures. Additionally, the extent of tissue growth into and around the catheter can also preclude the creation of additional apertures, for example, in situations where the tissue growth covers a substantial portion of the ventricular catheter. Another disadvantage of creating new apertures to repair an occluded ventricular catheter is that this method fails to prevent or reduce the risk of repeated obstructions.

Because attempts at flushing or repairing a blocked ventricular catheter are often futile and ineffective, occlusion is more often treated by replacing the catheter. Although this can be accomplished by removing the obstructed catheter from the ventricle, the growth of the choroid plexus and other tissues around the catheter and into the apertures can hinder removal and replacement of the catheter. Care must be exercised to avoid damage to the choroid plexus, which can cause severe injury to the patient, such as, for example, hemorrhaging. Not only do these procedures pose a significant risk of injury to the patient, they can also be very costly, especially when shunt obstruction is a recurring problem.

Accordingly, there exists a need for a shunt and a ventricular catheter that minimizes or eliminates the risk of blockage or obstruction of the catheter apertures, that increases the ease of revision surgery if the catheter is removed and reduces the need for repeated repair and/or replacement.

SUMMARY OF THE INVENTION

The present invention provides a shunt that includes a housing having an inlet, an outlet and a flow control mechanism disposed within the housing. A ventricular catheter is connected to the inlet of the housing. The catheter has a longitudinal length, a proximal end, a distal end, and an inner lumen extending therethrough. The inner lumen of the catheter includes at least two lumens at the distal end and has only one lumen at the proximal end. The catheter has one aperture corresponding to each of the at least two lumens located at the distal end of the catheter.

BRIEF DESCRIPTION OF THE DRAWING FIGURES

FIG. 3 is a cross-sectional view taken along lines 3-3 of FIG. 2 and looking in the direction of the arrows;

FIG. 4 is a cross-sectional view taken along lines 4-4 of FIG. 3 and looking in the direction of the arrows;

FIG. 4A is a cross-sectional view taken along lines 4A-4A of FIG. 3 and looking in the direction of the arrows;

FIG. 5 is a cross-sectional view taken along lines 5-5 of FIG. 3 and looking in the direction of the arrows;

FIG. 6 is a partial top view of a prior art ventricular catheter;

FIG. 7 is cross-sectional view taken along lines 7-7 of FIG. 6 and looking in the direction of the arrows;

FIG. 8A is a partial top view of the ventricular catheter according to the present invention; and FIG. 8B is a partial top view of the ventricular catheter according to the present invention.

FIG. 9 is a partial perspective view, with parts broken away, showing the interior of the ventricular catheter according to the present invention.

DETAILED DESCRIPTION OF THE PRESENT INVENTION

Referring now to FIGS. 1-5, 8A, 8B and 9 a shunt 10 and a ventricular catheter 12 in accordance with the present invention is illustrated.

Figure 1:
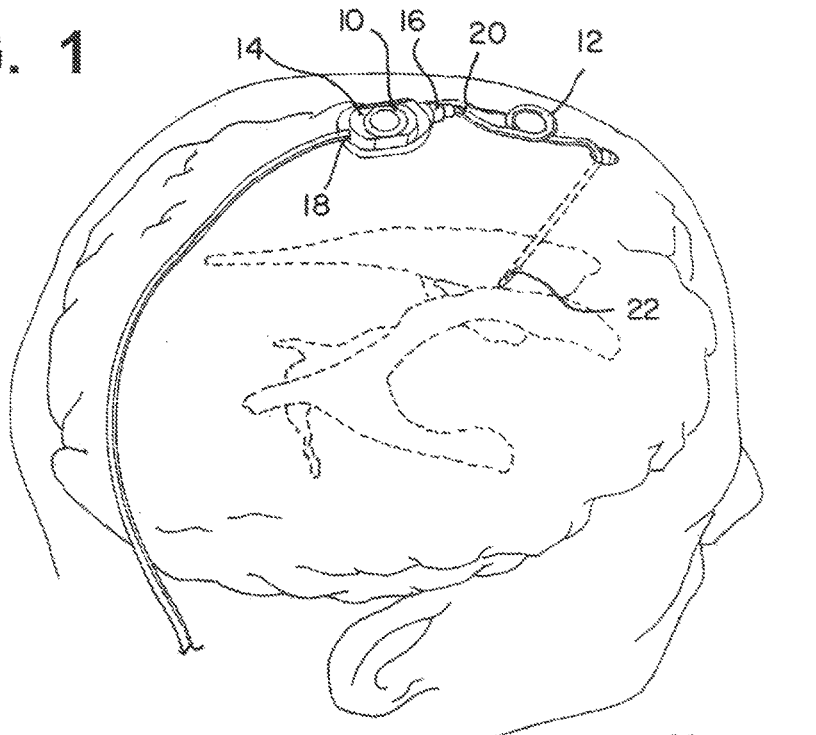
FIG. 1 is a top perspective view of the shunt and ventricular catheter according to the present invention.

As illustrated in FIG. 1, shunt 10 has a housing 14, which has an inlet 16, an outlet 18 and a flow control mechanism disposed therein. Ventricular catheter 12 is connected to inlet 16 of the housing. Catheter 12 has a longitudinal length, a proximal end 20, a distal end 22, and an inner lumen 24 extending therethrough. Inner lumen 24 is a single lumen at proximal end 20 of the catheter and is comprised of two or more lumens $24^1$, $24^{11}$, $24^{111}$, $24^{1111}$, etc. at the distal end 22 of catheter 12. Catheter 12 is preferably made of silicone. In addition, catheter 12 can be impregnated with antimicrobial antibiotics, such as the CODMAN® BACTISEAL® catheter, which is commercially sold by Codman & Shurtleff, Inc. of Raynham, Mass.

Ventricular catheter 12 has only one aperture 26 at distal end 22 of catheter 12 corresponding to each of the lumens $24^1$, $24^{111}$, $24^{1111}$, etc. There are preferably between 2 and 7 lumens, with only three and four lumens being shown in the drawing Figures for the sake of brevity. Of course, one skilled in the art would readily know how to make the ventricular catheter of the present invention with multiple lumens based on the present disclosure. Each tapering slit 30 receives cerebrospinal fluid (CSF) when in use. Each aperture 26 has an enlarged opening 28 at the distal end and transitions from the enlarged opening to a tapering slit 30 at the proximal end of the aperture. In some examples of the present invention, for each aperture 26, a portion 32 between the enlarged opening 28 and the tapering slit 30 is a slit 32 of constant thickness. Likewise, in other examples of the present invention, for each aperture 26, there may be no portion 32 between the enlarged opening 28 and the tapering slit 30. In addition, as illustrated in FIG. 9, for each aperture 26, a slit 42 of constant thickness can be disposed between the enlarged opening 28 and the proximal end of the aperture with no tapering slit being utilized. The entire aperture, from the enlarged opening 28 to the proximal end of tapering slit 30 is in fluid communication with its respective lumen $24^1$, $24^{111}$, $24^{1111}$, etc. The enlarged opening 28 of each aperture has a smooth concave inner surface 34, similar to a spoon shape.

The use of multiple lumens $24^1$, $24^{111}$, $24^{1111}$, etc. in accordance with the present invention help prevent complete occlusion of ventricular catheter 12. In the present invention, ventricular catheter 12 can only be completely occluded if all the lumens become blocked. In addition, because the transition from multiple lumens to a single lumen 24 occurs from about 0.5 to about 3.0 centimeters from the distal end of the ventricular catheter, any ingrowth of choroid plexus or ependymal tissue must extend beyond this junction to cause complete occlusion and interconnection of tissue from multiple apertures, which is unlikely to happen because of the length the tissue has to grow. The only other way that the choroid plexus or ependymal tissue would cause a complete occlusion is for the tissue to block each of the multiple lumens 24 beyond the slit 30, or to occlude the entire slit 30 and the aperture 26.

The slit lumen geometry is preferably tapered or purposely shaped to provide resistance to fluid flow through the slit that corresponds to the size of the pathway provided by the slit. The size of the slit opening distributes the pressure gradient over a larger distance and surface area than conventional ventricular catheters. Diffusing the pressure gradient diminishes the attractive fluid forces and diminishes areas of high fluid flow, thereby lessens the propensity for tissue ingrowth.

Referring now to FIGS. 8A and 8B of the present invention, tissue ingrowth 36 is illustrated. As can be seen, tissue ingrowth into aperture 26 will not interconnect with tissue ingrowth from another lumen. Thus, should the ventricular catheter 12 need to be removed, catheter 12 will be pulled back out and tissue ingrowth 36 can be removed from the lumen at the wider end of the taper or at the enlarged opening 28, as illustrated in FIG. 8B. In contrast, in the prior art, tissue ingrowth 36 can be rather difficult to remover from the ventricular catheter should the ventricular catheter 12 need to be removed, as discussed above.

Figure 2:
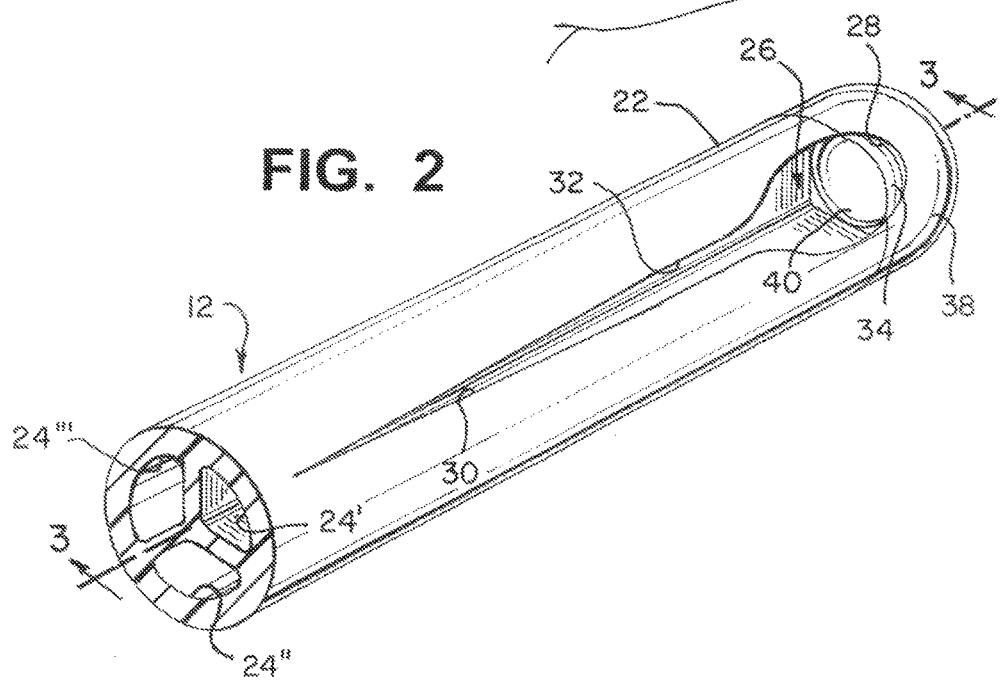
FIG. 2 is a partial perspective view, with parts broken away, showing the interior of the ventricular catheter according to the present invention.

Referring now to FIGS. 2 and 3, ventricular catheter 12, has a blunt distal end 38 to permit the catheter to be introduced into the brain without damaging brain tissue. In addition, an inner concave surface 40 is sized to receive a stylet for use in introducing the catheter.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A method of removing an obstruction from within an inner lumen of a ventricular catheter of a shunt system when the ventricular catheter is implanted in a brain, the ventricular catheter having a longitudinal length, a proximal end, a distal end, and the inner lumen extending therethrough, the inner lumen of the catheter being comprised of at least two lumens at the distal end and being comprised of only one lumen at the proximal end, the catheter having an aperture adjacent to the distal end corresponding to each of the at least two lumens; wherein each aperture has an enlarged opening at the distal end and transitions from the enlarged opening to a tapering slit only at the proximal end of the aperture, the method comprising the steps of:

accessing the ventricular catheter; and moving the ventricular catheter in the proximal direction such that the obstruction is removed from the ventricular catheter inner lumen at the enlarged opening at the distal end.

2. A method of removing an obstruction from within an inner lumen of a ventricular catheter of a shunt system when the ventricular catheter is implanted in a brain, the ventricular catheter having a longitudinal length, a proximal end, a distal end, and the inner lumen extending therethrough, the inner lumen of the catheter having an aperture that has an enlarged opening at the distal end and transitions from the enlarged opening to a tapering slit only at the proximal end of the aperture, the method comprising the steps of:

accessing the ventricular catheter; and moving the ventricular catheter in the proximal direction such that the obstruction is removed from the ventricular catheter inner lumen at the enlarged opening at the distal end.

\* \* \* \* \*